United States Patent
Cook et al.

[11] Patent Number: 6,152,150
[45] Date of Patent: Nov. 28, 2000

[54] METHOD OF STAIN REMOVAL USING A DRY ZEOLITE CONTAINING COMPOSITION

[75] Inventors: John B. Cook, Phoenixville, Pa.; Gary J. Calton, Elkridge, Md.

[73] Assignee: OdorPro, Inc., Elkridge, Md.

[21] Appl. No.: 09/366,669

[22] Filed: Aug. 3, 1999

[51] Int. Cl.$^7$ .................................................. B08B 7/00
[52] U.S. Cl. ................................ 134/7; 134/6; 134/34; 134/36; 134/40; 134/42; 510/130; 510/138; 510/139; 510/158; 510/475; 510/507; 424/489
[58] Field of Search ............................. 134/6, 7, 34, 36, 134/401, 42; 510/130, 138, 139, 158, 507, 475; 424/489

[56] References Cited

U.S. PATENT DOCUMENTS

| | | | |
|---|---|---|---|
| 3,247,195 | 4/1966 | Kerr et al. | 260/242 |
| 4,098,713 | 7/1978 | Jones | 252/89 |
| 4,210,416 | 7/1980 | Plapper et al. | 8/139.1 |
| 4,719,030 | 1/1988 | Williams et al. | 252/133 |
| 4,864,060 | 9/1989 | Karalis et al. | 564/292 |
| 5,041,243 | 8/1991 | Joshi | 252/534 |
| 5,139,782 | 8/1992 | Jung | 424/401 |
| 5,266,237 | 11/1993 | Freeman et al. | 252/542 |
| 5,458,809 | 10/1995 | Fredj et al. | 252/542 |
| 5,540,855 | 7/1996 | Baillely et al. | 510/276 |
| 5,643,863 | 7/1997 | Guerin et al. | 510/466 |
| 5,686,402 | 11/1997 | Gutierrez et al. | 510/361 |
| 5,707,950 | 1/1998 | Kasturi et al. | 510/320 |
| 5,736,503 | 4/1998 | Vinson | 510/481 |
| 5,833,972 | 11/1998 | Wood et al. | 424/76.5 |
| 5,837,670 | 11/1998 | Hartshorn | 510/490 |
| 5,869,027 | 2/1999 | Wood et al. | 424/76.5 |
| 5,958,858 | 9/1999 | Bettiol et al. | 510/351 |
| 6,004,584 | 12/1999 | Peterson et al. | 424/489 |

FOREIGN PATENT DOCUMENTS 55116798  9/1980  Japan.

*Primary Examiner*—Sharidan Carrillo
*Attorney, Agent, or Firm*—Beverly J. Artale

[57] ABSTRACT

A dry zeolite containing composition is used in a method for removing grease and/or oil stains from the human body is disclosed. In accordance with the method, zeolites having an average particle size of about 0.5 mm or less provide superior performance to remove grease and oil stains from the skin. Stain removing activities of the zeolite compositions may be enhanced by the addition of an imide.

13 Claims, No Drawings

METHOD OF STAIN REMOVAL USING A DRY ZEOLITE CONTAINING COMPOSITION

FIELD OF THE INVENTION

This invention relates to novel compositions for removing oil and grease stains from the human body. More particularly, this invention relates to a method of using zeolite having a specified particle size for the removal of oil and grease stains from the human body. The zeolite is used alone or in combination with an imide.

BACKGROUND OF THE INVENTION

The removal of greasy/oil soils quickly and efficiently can be problematic for a number of substrates. In particular, the removal of grease and oil stains from the human body, especially the extremities thereof, presents a particular challenge.

Zeolites are commonly used in detergents for their "builder" capabilities. U.S. Pat. No. 5,736,503, discloses laundry and dishwashing detergent compositions which provide spontaneous emulsification of grease. The patent discloses the use of zeolite as a "builder". Improved grease and oil removal properties of the composition are attributable to the use of nonionic surfactants, non conventional detergent surfactants, conventional ethoxylated nonionic and sulfated or sulfonated anionic surfactants.

U.S. Pat. No. 4,098,713 discloses the use of complex aluminosilicates, i.e., zeolite-type materials, as presoaking/washing adjuvants to soften water, i.e., remove $Ca^{++}$ hardness.

Zeolite has not heretoafore been reported as the active stain removing agent in a grease and oil removing composition.

SUMMARY OF THE INVENTION

It has now been surprisingly discovered that zeolites having an average particle size of about 0.5 mm or less in diameter provide superior performance to remove grease and oil stains from the human body. This phenomenon is particularly noteworthy in the case of removing grease and oil stains from the hands. While not intending to be limited by an particular theory, it appears that the use of the small particle size or "powdered" zeolite enables the zeolite particles to penetrate the indentations or crevices in the skin, thereby directly contacting the oil/grease stain. It has further been discovered that the performance of zeolite to remove grease and oil from the body is greatly enhanced by the addition of an imide.

Accordingly, it is an advantage of the present invention to provide novel compositions having a high affinity for the removal of oil and grease stains from the human body, especially the extremities thereof.

It is also an advantage of the present invention to provide novel grease and oil stain removing compositions which uses zeolite or a zeolite/imide mixture as the active stain removing agent.

It is a further advantage of the invention to provide a method for removing oil and grease stains from the human body using said zeolite containing compositions.

These and other advantages of the present invention are described in more details below.

DETAILED DESCRIPTION OF THE EMBODIMENTS

Zeolites useful to prepare composition in accordance with the present invention include naturally occurring or synthetic zeolites. Zeolites, whether natural or synthetic, are characterized by an aluminosilicate tetrahedral framework, and have ion exchangeable large cations and loosely held water molecules permitting reversible dehydration. The general formula for a zeolite is as follows: $MO.Al2O_3.nSiO_2.xH_2O$, where M is Na, K, Ca, Sr or Ba and n and x are integers.

The oxygen atoms in the framework of the zeolite are each shared by two tetrahedrons, thus, the (Si, Al):O ratio is exactly 1:2. The amount of large cations present is dependent on the aluminum to silicon ratio and the formal charge of these large cations. The large cations, which are coordinated by framework oxygens and water molecules, reside in large cavities in the crystal structure. These cavities and channels may even permit the selective passage of organic molecules.

A partial listing of natural zeolites is given in Table 1.

TABLE 1

| Group | Name | Formula |
| --- | --- | --- |
| Analcime | Analcime | $Na(Al_{16}Si_{32}O_{96}).16H_2O$ |
|  | Wairakite | $Ca_{16}(Al_{16}Si_{32}O_{96}).16H_2O$ |
|  | Pollucite | $Cs_{32}(Al_{16}Si_{32}O_{96}).16H_2O$ |
| Sodalite | Sodalite | $Na_6(Al_6Si_6O_{24}).2NaCl$ |
|  | Faujasite | $(Na_2, Ca, Mg)_{29} ((Al_{58}Si_{134}O_{384}).240H_2O$ |
| Chabazite | Chabazite | $Ca6(Al_{12}Si_{24}O_{72}).40H_2O$ |
|  | Gmelinite | $(Na_2, Ca)_4 [Al_8Si_{16}O_{48}).24H_2O$ |
|  | Erionite | $(Na_2Ca)_{3.5} K_2[Al_9Si_{27}O_{72}).27H_2O$ |
|  | Offretite | $(Ca,Mg)_{1.5} K[Al_4Si_{14}O_{36}].14H_2O$ |
|  | Levyne | $Ca_9(Al_{18}Si_{36}O_{108}).50H_2O$ |
| Natrolite | Natrolite | $Na_{16}(Al_{16}Si_{24}O_{80}).16H_2O$ |
|  | Scolecite | $Ca_{16}(Al_{16}Si_{24}O_{80}).16H_2O$ |
|  | Mesolite | $Na_{16}Ca_{16}(Al_{16}Si_{24}O_{80}).64H_2O$ |
|  | Edingtonite | $Ba_2(Al_4Si_6O_{20}).8H_2O$ |
|  | Thomsonite | $Na_4Ca_8(Al_{20}Si_{20}O_{80}).24H_2O$ |
|  | Gonnardite | $Na_{6.42}, K_{0.01}, Ca_{1.5}Al_{9.22}OSi_{110.43}O_{40}.12.37H_2O$ |
| Phillipsite | Phillipsite | $K_2(Ca, Na_2)_2(Al_6Si_{10}O_{32}).12H_2O$ |
|  | Harmontome | $Ba_2(Al_4Si_{12}O32).12H_2O$ |
|  | Gismondine | $Ca_4(Al_8Si_8O_{32}).16H_2O$ |
|  | Garronite | $(NaCa_2)_5(Al_6Si_{10}O_{32}).13H_2O$ |
| Mordenite | Mordenite | $Na_8(Al_8Si_{40}O_{96}).24H_2O$ |
|  | Diachiardite | $Na_5(Al_5Si_{19}O_{48}).12H_2O$ |
| Other | Clinoptilolite | $Na_6(Al_6Si_{30}O_{72}).72H_2O$ |
|  | Heulandite | $Ca_4(Al_8Si_{28}O_{72}).24H_2O$ |
|  | Brewsterite | $(Sr, Ba)_2(Al_4Si_{12}O_{32}).10H_2O$ |
|  | Epistilbite | $Ca_3(Al_6Si_{18}O_{48}).16H_2O$ |
|  | Stilbite | $Na_4Ca_8(Al_{20}Si_{52}O_{144}).56H_2O$ |
|  | Yugawaralite | $Ca_2(Al_4Si_{12}O_{32}).8H_2O$ |
|  | Laumontite | $Ca_4(Al_8Si_{16}O_{48}).16H_2O$ |
|  | Ferrierite | $Na_2Mg_2(Al_6Si_{30}O_{72}).18H_2O$ |
|  | Paulingite | $(K_2, Ca, Na_2)_{76} [Al_{152}Si_{520}O_{1344}]\cdot7H_2O$ |

Prior art techniques have resulted in the formation of a great variety of synthetic zeolites. These zeolites have come to be designated by letter or other convenient symbols, as illustrated by zeolite A (U.S. Pat. No. 2,882,243), zeolite X (U.S. Pat. No. 2,882,244), zeolite Y (U.S. Pat. No. 3,130, 007), zeolite ZK-5 (U.S. Pat. No. 3,247,195), zeolite ZK-4 (U.S. Pat. No. 3,314,752), zeolite ZSM-5 (U.S. Pat. No. 3,702,886), zeolite ZSM-11 (U.S. Pat. No. 3,709,979), zeolite ZSM-12 (U.S. Pat. No. 3,832,449), zeolite ZSM-20 (U.S. Pat. No. 3,972,983), ZSM-23 (U.S. Pat. No. 4,075, 842), ZSM-35 (U.S. Pat. No. 4,016,245), ZSM-38 (U.S. Pat. No. 4,046,859), to name a few.

While any zeolite may be useful to prepare the oil and grease removing compositions of the invention, preferred zeolites are Clinoptilolite, Chabazite, Mordenite, Y, 4A, 5A, P, ZSM-5, 3A, 13X, and mixtures thereof. It is also within the scope of this invention to use calcined zeolites such as 4A, Y, Mordenite, Silicalite and combinations thereof.

Zeolite is used in the invention composition in the form of particles having an average diameter of about 0.5 mm or less. Preferably, the particles have an average diameter ranging from about 0.1 mm or less. Most preferably, the zeolite particles have an average diameter ranging from about 0.06 mm or less.

Compositions in accordance with the invention comprise at least one zeolite, optionally mixed with at least one imide. Zeolite is present in the compositions in an amount ranging from about 50% to about 100% by weight based on the total weight of the composition mixture. Preferably, the amount of zeolite is about 90% to about 99.9% of the total weight of the composition.

Any imide may be useful to prepare the stain removing compositions of the invention, however, preferred imides are disclosed in U.S. Pat. No. 5,833,972 and U.S. Pat. No. 5,869,027, herein incorporated by reference. In the most preferred embodiment, the imide is a polyimide selected from the group consisting of polysuccinimide, polyglutarimide, copolymers and terpolymers of polysuccinimide and polyglutarimide, and combinations thereof.

The imide may be present in the composition in an amount up to about 50% by total weight of the oil and grease removing composition. Preferably, the imide is present in an amount ranging from about 0.05% to about 10% by weight of the total composition. Most preferably, the oil and grease removing composition of the invention comprises an imide content of about 0.1% to about 5% by weight of the total composition.

Stain removing compositions in accordance with the present invention are prepared from a least one zeolite optionally mixed with at least one imide using conventional mixing techniques. The stain removing composition may be used in the form of a slurry, a paste, a suspension or a powder. Preferably, compositions of the invention are used in the form of a generally dry, free-flowing powder.

Compositions according to the invention may comprise one or more optional constituents including, but not limited to: buffers and pH adjusting agent, fragrances and deodorizing agent, filler and carriers including inorganic salts, ultraviolet absorbents, germicides, preservatives, fillers including talc and naturally occurring or synthetic clays, further scattering and spreading promoters, antisoiling or resoiling inhibitors, chelating agents as well as others constituents known to the art but not elucidated hereinabove. Such constituents as described above include known art compositions, including those described in Kirk-Othmer, *Encyclopedia of Chemical Technology*, $33^{rd}$ Ed., Vol. 22, pp. 346–387.

Such optional constituents may be included in the compositions in an amount which does not undesirably detract from the advantageous features provided by the essential constituents forming the inventive compositions. Preferably, the total weight of such optional constituents does not exceed about 25% of the total weight of the composition, and more preferably, does not exceed about 10% by weight of the total weight of the composition according to the invention.

In accordance with the process of the invention, a grease or oil stain on the skin is removed by contacting the skin at the locus of the oil and/or grease stain with an effective stain removing amount of formulations according to the invention, applying sufficient pressure and agitation to the treated area to provide optimum contact between the zeolite or zeolite/imide mixture and the oil and/or grease stain, and thereafter washing the locus of the treated area with a mild detergent or soap and water to remove the stain.

Formulations of the invention may be applied to the locus of oil and grease stain by hand or by means of a suitable appliance. In general, invention formulations are applied in any quantity sufficient to completely cover the stain. Pressure and agitation is applied to the treated area in an amount and for a period of time sufficient to allow the stain removing compositions to penetrate the crevices or indentations in the skin, thereby facilitating removal of the desired stain.

In order to further illustrate the present invention and the advantages thereof, the following examples are given. It is understood that the examples are intended only as illustrative and are not intended to be limiting in nature.

EXAMPLE 1

A volunteer systematically soiled his fingers with a dirty oil/grease mixture taken from the valve cover of a used automobile engine. The oil/grease mixture was black in color, sticky and filled the fingerprints and pores in the skin of the fingers. Various zeolites, imides and mixtures thereof were applied on the fingers in an amount sufficient to completely cover the oil/grease mixture by visual observation and rubbed into the skin with a pressure sufficient to insert the zeolite, imide or zeolite/imide composition into the crevices of the skin.

Each finger was thereafter washed with hand soap and water. Each of the zeolite used in this experiment passed through a 400 mesh screen. Results are recorded in Table 2 below.

TABLE 2

| Formulation | % removal with soap & water after treatment |
| --- | --- |
| Clinoptilolite | 80% |
| Clinoptilolite with polysuccinimide, (3%) | 90% |
| zeolite P plus polysuccinimide, (3%) | 99+% |
| polysuccinimide | 75% |
| zeolite 13X | 83% |
| zeolite 4A | 78% |
| zeolite 5A | 90% |
| zeolite 3A | 70% |
| soap and water only | 50% |

EXAMPLE 2

Particle Size

A sample of clinoptilolite was separated into sizes of chips (0.5 to 2 mm diameter), grains (0.044 to 0.5 mm diameter) and powder particles (less than 0.044 mm diameter). These materials were tested for oil removal from a volunteer's hands (stained in the same manner as in described in Example 1 above). Oil removal by chips was ineffective as less than 50% of the oil was removed and the chips were painful when rubbed in the hands. Grains were effective at removing the oil (50–70%) but still caused pain when rubbed in the hands. The powder (less than 0.044 mm diameter) was extremely effective at removing the oil (greater than 80%).

It will be apparent to those skilled in the art that the examples and embodiments described herein are by way of illustration and not of limitation, and that other examples may be utilized without departing from the spirit and scope of the present invention, as set forth in the appended claims.

We claim:

1. A method for removing oil and grease stains from the skin of a human body, said method comprising providing a stain on the surface of the skin of a human body, applying to the stain an effective stain removing amount of a composition comprising at least one zeolite having a particle size of less than about 0.5 mm average diameter, wherein said composition is applied to the stain in a dry form, permitting the dry composition to remove the stain from the skin, and thereafter removing the dry composition from the surface of the skin.

2. The method of claim 1 wherein said zeolite has a particle size of less than about 0.1 mm average diameter.

3. The method of claim 1 wherein said zeolite has a particle size of less than about 0.06 mm average diameter.

4. The method of claim 1 wherein the zeolite is selected from the group consisting of Chabazite, Clinoptilolite, Mordenite, zeolite Y, zeolite 4A, zeolite 5A, zeolite P, ZSM-5, Silicalite and mixtures thereof.

5. The method of claim 1 wherein the dry composition further comprises at least one imide.

6. The method of claim 4, wherein the zeolite is 5A.

7. The method of claim 4 wherein the zeolite is zeolite P.

8. The method of claim 4 wherein said zeolite is zeolite 4A.

9. The method of claim 4 wherein said zeolite is Clinoptilolite.

10. The method of claim 5 wherein said at least one imide is a polyimide.

11. The method of claim 10 wherein the polyimide is selected from the group consisting of polysuccinimide, copolymers of polysuccinimide, terpolymers of polysuccinimide, polyglutarimide, copolymers of polyglutarimide, terpolymers of polyglutarimide, and mixtures thereof.

12. The method of claim 11 wherein said polyimide is polysuccinimide.

13. The method of claim 11 wherein said polyimide is a copolymer of polysuccinimide.

* * * * *